United States Patent [19]

Ariga et al.

[11] Patent Number: 4,797,421
[45] Date of Patent: Jan. 10, 1989

[54] ANTIOXIDANT COMPRISING PROANTHOCYANIDIN AS PRINCIPAL COMPONENT

[75] Inventors: Toshiaki Ariga, Noda; Ikunori Koshiyama, Nagareyama; Danji Fukushima, Omiya, all of Japan

[73] Assignee: Kikkoman Corporation, Noda, Japan

[21] Appl. No.: 102,805

[22] Filed: Sep. 22, 1987

Related U.S. Application Data

[63] Continuation of Ser. No. 798,620, Nov. 15, 1985, abandoned.

[51] Int. Cl.$^4$ ............................ A23D 5/04; A61K 7/00
[52] U.S. Cl. .................................... 514/844; 514/873; 549/382; 549/399; 426/545
[58] Field of Search ................ 426/545; 549/382, 399; 536/8; 514/844, 873

[56] References Cited

U.S. PATENT DOCUMENTS 3,270,003  8/1966  Blaricom et al. ................... 549/399

FOREIGN PATENT DOCUMENTS

| 4358M | 9/1966 | France | 549/400 |
| 56-92283 | 7/1981 | Japan | 549/400 |
| 58-103383 | 6/1983 | Japan | 549/399 |
| 58-154585 | 9/1983 | Japan | 549/382 |
| 58-154571 | 9/1983 | Japan | 549/399 |
| 59-638 | 4/1984 | Japan . | |
| 1155601-A | 4/1981 | U.S.S.R. | 549/399 |

OTHER PUBLICATIONS

Agricultural Biological Chemistry, 45 (12) pp. 2709–2712.
Journal of Chemical Society, Perkin I, pp. 2663–2671 (1974).
Phytochemistry, 22 (1), pp. 275–281 (1983).
Arch. Pharmaz., pp. 666–673 (1971).
Phytochemistry, 21 (2) pp. 429–432 (1982).
Photochemistry, 22 (1), pp. 237–241 (1983).
J. Sci. Food Agric., vol. 34, pp. 62–14 72 (1983).
Ann. Chim. (Rome), vol. 57, pp. 1364–1371 (1967).
J. Sci. Food Agric., vol. 29, pp. 471–477 (1978).
Journal of Institute Brewing, vol. 89, pp. 424–431 (1983).
Journal of Institute Brewing, vol. 80, pp. 188–192 (1974).

Primary Examiner—Nicky Chan
Attorney, Agent, or Firm—Banner, Birch, McKie & Beckett

[57] ABSTRACT

An antioxidant containing a proanthocyanidin which is at least one member selected from the group consisting of those dimers to decimers which have bonded thereto as a structural unit a flavan-3-ol or flavan-3,4-diol represented by the general formula:

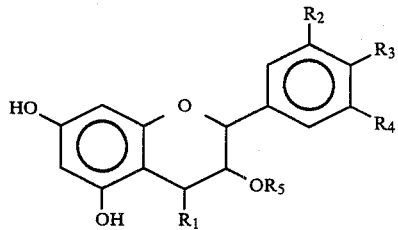

(wherein $R_1$ is hydrogen or a hydroxyl group, $R_2$, $R_3$ and $R_4$ are each hydrogen, a hydroxyl group or a methoxy group, and $R_5$ is hydrogen, a galloyl group or a glycopyranosil group).

4 Claims, No Drawings

ANTIOXIDANT COMPRISING PROANTHOCYANIDIN AS PRINCIPAL COMPONENT

This application is a continuation of application Ser. No. 06/798,620 filed Nov. 15, 1985, now abondaned.

BACKGROUND OF THE INVENTION

1. Field of the Invention

This invention relates to an antioxidant for foods, pharmaceuticals, cosmetics and the like of which the main component is a natural plant extract. 2. Description of the Prior Art Oils and fats, or foods, pharmaceuticals, cosmetics, etc., containing oils and/or fats are liable to air oxidation which badly affects their quality, so that an antioxidant is used for preventing such oxidation.

The antioxidants which have been generally used for said purpose are grouped into two types: synthetic antioxidants such as butyl hydroxytoluene (BHT), butyl hydroxyanisole (BHA), etc., and natural antioxidants such as dl-α-tocopherol, guaiac, etc.

Synthetic antioxidants have the problem in the aspect of safety because of their strong toxicity, while natural antioxidants have the problem of weak effect or short duration of effect. Therefore, the development of a natural antioxidant having no problem over safety in use and also having excellent effect and long duration of effect has been required.

SUMMARY OF THE INVENTION

In the course of the studies on proanthocyanidins extracted from various plants, the present inventors found that the various types of proanthocyanidins have a strong antioxidant action and completed the present invention based on such finding.

Thus, the present invention provides an antioxidant comprising a proanthocyanidin as the principal component.

DETAILED DESCRIPTION OF THE INVENTION

The proanthocyanidins provided according to this invention are a group of the compounds having a condensed tannin found in various plants, that is, flavan-3-ol or flavan-3,4-diol which is bonded as a structural unit by condensation or polymerication. These compounds, upon undergoing an acid treatment, produce anthocyanidins such as cyanidin, delphinidin, pelargonidin, etc., hence are given the name of "proanthocyanidin".

Said proanthocyanidins, therefore, include all of the polymers ranging from dimers to decimers or even higher-order polymers of said structural unit, such as procyanidin, prodelphenidin, propelargonidin, etc., and their stereoisomers. In this invention, however, it is preferred to use those proanthocyanidins which are di- to decimers, more preferably di- to tetramers having as their structural unit a flavan-3-ol or flavan-3,4-diol represented by the general formula:

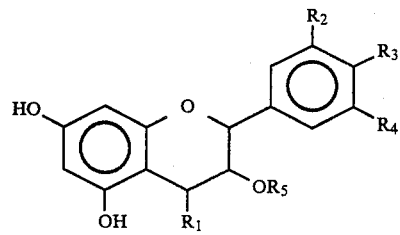

(wherein $R_1$ is hydrogen or a hydroxyl group, $R_2$, $R_3$ and $R_4$ are hydrogen, a hydroxyl group or a methoxyl group, and $R_5$ is hydrogen, galloyl or glycopyransyl) because of their excellent solubility in water and effect.

These proanthocynidins are characterized typically by their outstandingly strong antioxidant action in comparison with the monomer catechin which is a structural unit of said proanthocyanidin and which is also known to have an antioxidant action.

Said proanthocyanidins of their invention can be obtained from a known process: extracting various kinds of plant body with a solvent and fractionating the extract by liquid chromatography or other means, or treating a secondary product such as fruit wine, beer, etc., using plant essence as raw material with a selective adsorbent of proanthocyanidin, concentrating the proanthocyanidin fraction and further fractionating the concentrate by a counter-current distribution method, liquid chromatography or other means.

Some typical examples of proanthocyanidins obtained by fractionating a plant extract are shown below.

A dimeric procyanidin B-2 represented by the formula (1):

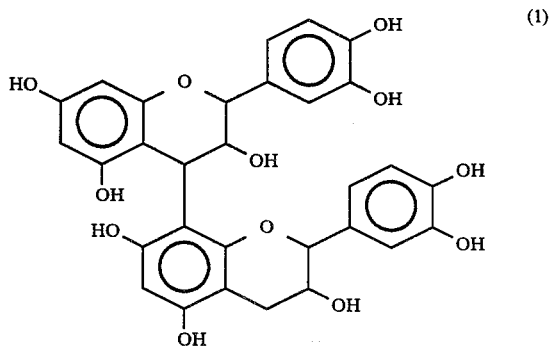

and a dimeric procyanidin represented by the formula (2):

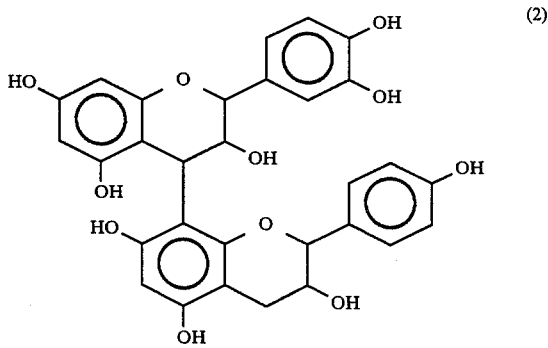

can be obtained by fractionating a 70% aqueous acetone extract of azuki beans (Vigna angularis Ohwi et Ohashi) by liquid chromatography using polyamide C-200 and Sephadex LH-20 columns according to the method of the present inventors shown in Agricultural Biological Chemistry, Vol. 45, pp. 2709–2712 (1981).

A dimeric proanthocyanidin A-2 represented by the formula (3):

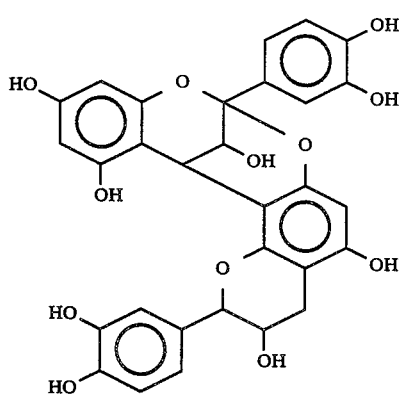

can be obtained according to the method of D. Jacques et al. shown in Journal of Chemical Soceity, Perkin I. 2663–2671 (1974), by using shells or horse chestnut (*Aesculus hippocastanum*) as starting material.

A dimeric procyanidin represented by the formula (4):

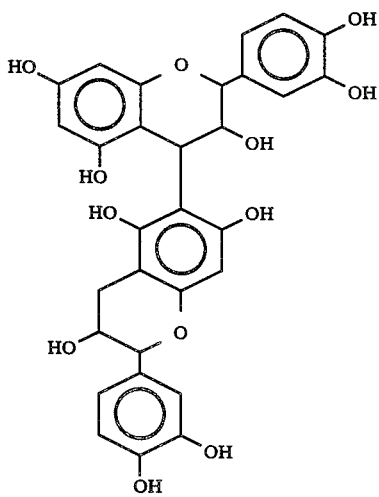

can be obtained according to the method of R. W. Hemingway et al. shown in Phytochemistry, Vol. 22, pp. 275–281 (1983), by using bark of pine (Loblolly pine).

A dimeric prodelphinidin represented by the formula (5):

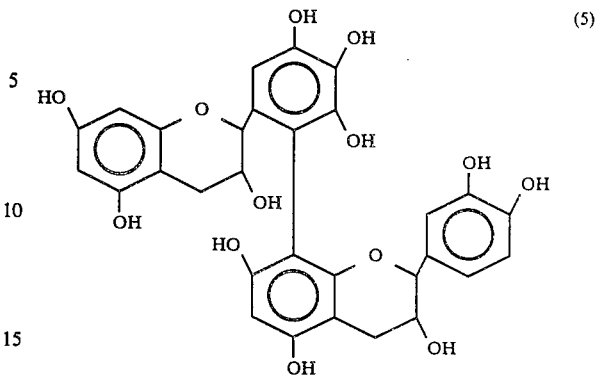

can be obtained according to the method of Byung-Zun Ahn et al. shown in Arch. Pharmaz., pp. 666–673 (1971) by using bark of oak.

Two types of dimeric procyanidin B-1 gallates represented by the formula (6):

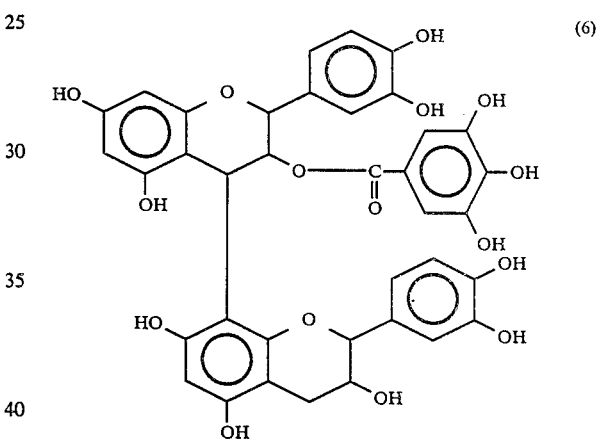

and the formula (7):

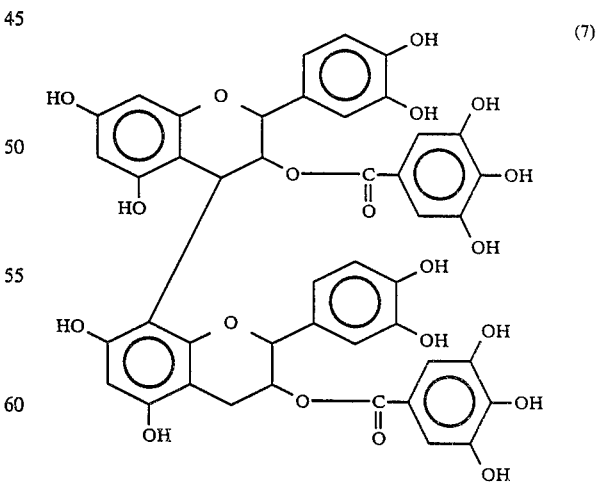

can be obtained according to the method of Nonaka et al. shown in Phytochemistry, Vol. 21, pp. 429–432 (1982), by using root of a knotgrass (*Polygonum multiflorum*) as starting material.

A dimeric prodelphinidin B-2 gallate represented by the formula (8):

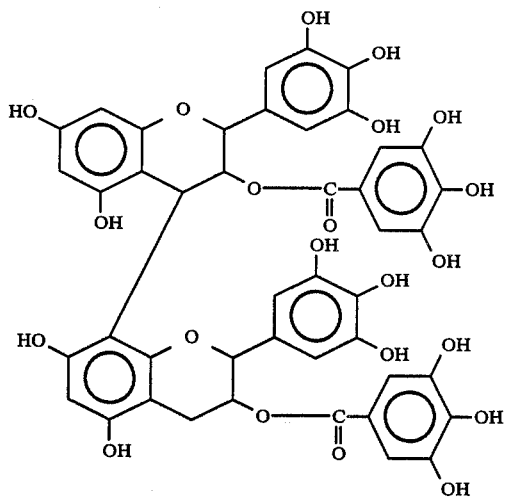

can be obtained according to the method of Nonaka et al. shown in Phytochemistry, Vol. 22, pp. 237–241 (1983) by using bark of a myrica (myricarubra) as starting material.

A dimeric propelargonidin represented by the formula (9):

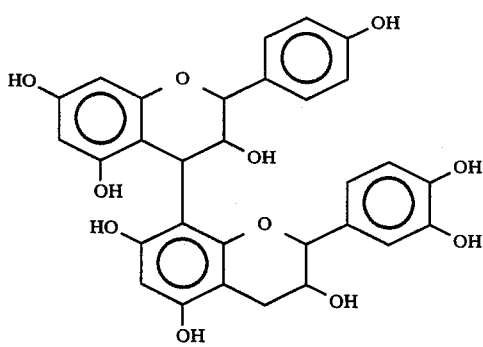

and a trimeric prodelphinidin represented by the formula (10):

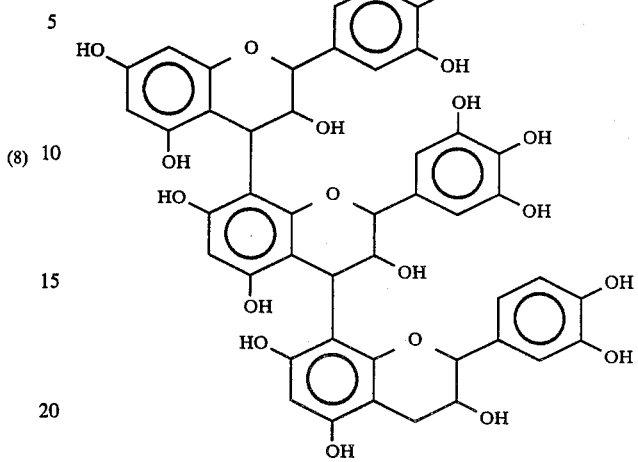

can be obtained from barley and malt according to the method of I. McMurrough et al. shown in J. Sci. Food Agric., Vol. 34, pp. 62–72 (1983).

A dimeric procyanidin B-4 rhamnoside represented by the formula (11):

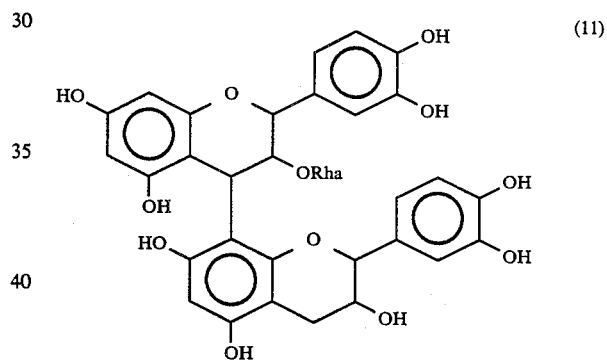

wherein RHa is rhamnose
can be obtained from the cortex of Kandellia according to the method disclosed in Japanese Patent Application Kokai (Laid-Open) No. 59638/84.

A propelargonidin represented by the formula (12):

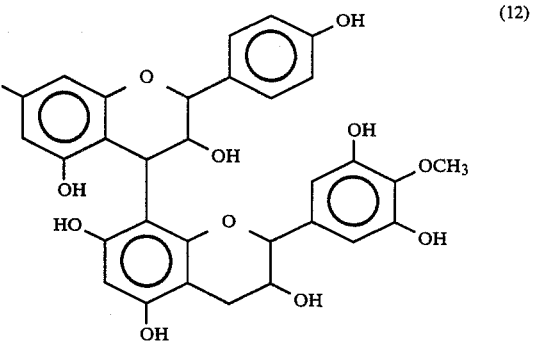

can be obtained from the root skin of ouratea according to the method of F.D. Monache et al. shown in Ann. Chim. (Rome), Vol. 57, pp. 1364–1371 (1967).

As regards the proanthocyanidins obtainable by fractionating a selective adsorbent-treated concentrate of a secondary product from a plant material, for example a tetrameric proanthocyanidin represented by the formula (13):

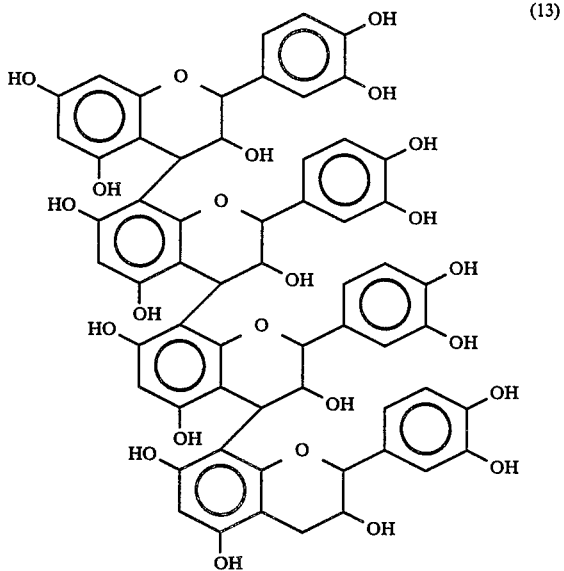

can be obtained by first preparing a concentrate of a proanthocyanidin obtained by treating cider by Sephadex LH-20 and then fractionating said concentrate by a counter-current distribution method using ethyl acetate and water or by liquid chromatography on a Sephadex LH-20 column, according to A.G.H. Lea's method shown in Journal of Science of Food Agriculture, Vol. 29, pp. 471-477 (1978).

Among said proanthocyanidins, for example the dimeric procyanidins B-3 and B-4 represented by the formula (1) can be obtained by a synthetic method using dihydroquercetin and catechin or epicatechin as starting material according to the method of G. Fonknechten et al. shown in Journal of Institute Brewing, Vol. 89, pp. 424-431 (1983), or the method of R. Eastmond shown in Journal of Institute Brewing, Vol. 80, pp. 188-192 (1974), and the thus obtained proanthocyanidins are also usable in this invention.

In the present invention, said proanthocyanidins are used as an antioxidant.

In use of said proanthocyanidins in this invention, any of said proanthocyanidins, isolated and purified, is added, either in the form as it is or after dissolved in water, an alcohol or an alcohol solution, to an oil or fat or products containing an oil and/or fat such as foods, pharmaceuticals, cosmetic preparations, and lubricating oils, or rubbers, plastics, etc., directly or to a base material thereof in an amount of 0.001-2% by weight. The proanthocyanidins used in this invention may not necessarily be isolated and purified; mixtures substantially composed of said proanthocyanidins can be also used in this invention provided that the amount of the proanthocyanidin used falls within the above-defined range. In case the proanthocyanidin used is not easily dissolved, a surface active agent may be added to increase the effect of the invention.

Shown below are the preparation examples of proanthocyanidins in accordance with this invention and the effect of these proanthocyanidins for preventing oxidation of fats and oils when these proanthocyanidins were added and dissolved directly in fats and oils as an antioxidant.

Preparation Example 1

1 kg Of fresh bark of Aesculus hippocastanum was ground with 3 litres of methanol (×2) in a Waring blender and extracted to obtain 5 liters of an aqueous methanol extract. This extract was washed with 5 liters of petroleum ether (×3) and concentrated under reduced pressure at a temperature below 30° C. to obtain 100 ml of a concentrated extract. The latter was then dissolved in 400 ml of distilled water and extracted with 300 ml of ethyl acetate (×8) and the resulting extract was concentrated under reduced pressure at a temperature below 30° C. to obtain 20 g of a crude phenolic extract. This was further dissolved in methanol and subjected to liquid chromatography on a column packed with polyamide resin (Polyamide Woelm) with methanol serving as developing solvent, and the resulting preparation was pipetted 15 ml each into 400 test tubes.

Of these samples, fractions 19-152 containing procyanidin were collected, concentrated and evaporated to dryness to obtain 4.8 g of crude procyanidin fraction.

This crude procyanidin fraction was dissolved in ethanol, subjected to liquid chromatography on a column (60 cm×2.5 cm$\phi$) packed with Sephadex LH-20 with ethanol serving as developing solvent and pippeted 15 ml each into 200 test tubes.

Of these samples, fractions 70-85 were collected concentrated and evaporated to dryness, whereby 0.96 g of yellowish white powder of a dimer procyanidin B-2 represented by the above-shown formula (1) was obtained. Also, by similarly concentrating and evaporating to dryness the fractions 85-160, there was obtained 2.31 g of yellowish white powder of a dimeric procyanidin A-2 represented by the formula (2).

PREPARATION EXAMPLE 2

1 kg Of barley (Hordeum vulgare) was ground to a grain size below 12 mesh, added with 4 liters of 75% aqueous acetone, stirred at room temperature for 3 hours and extracted. The extract was saturated with sodium chloride and shaken to separate it into an acetone layer and a water layer, and the acetone layer was concentrated to 150 ml under reduced pressure at 25° C.

This concentrated acetone layer was freeze-dried and extracted with 25 ml of methanol (×4), and the extract was further concentrated to 10 ml and fractionated by liquid chromatography using two-stage columns (20 cm×2.5 cm$\phi$ and 100 cm×2.5 cm$\phi$) packed with Sephadex LH-20.

Fractionation was carried out by using methanol as developing solvent, removing the first-stage column after first 500 ml of methanol has been flown, then flowing another 500 ml of methanol, removing the eluted fraction, then further flowing 1.5 liter of methanol, collecting the eluate and pipetting it 10 ml each into 150 test tubes.

Of these samples, fractions 60-74 were collected, concentrated and evaporated to dryness, producing 85 mg of yellowish white powder of a dimer prodeliphindin B-3 represented by the formula (5). Also, by collecting, concentrating and evaporating to dryness the fractions 75-90, there was obtained 48 mg of yellowish white powder of a trimeric prodelphinidin represented by the formula (10).

PREPARATION EXAMPLE 3

1 ml Of cider was filtered by using a column (3.2 cm$\phi \times$10 cm) packed with Sephadex LH-20 and polyphenol was adsorbed on the column. The column was washed with 250 ml of 20% aqueous methanol and eluted with 200 ml of 75% aqueous acetone, and the eluate was concentrated and evaporated to dryness to obtain 3.6 g of crude polyphenol fraction.

This was further fractionated into eight fractions 0–7, by a counter-current distribution method using ethyl acetate and water, and fraction 2 was concentrated and evaporated by dryness and again subjected to similar fractionation by the counter-current distribution method. Likewise, fraction 2 was concentrated and evaporated by dryness to obtain 120 mg of yellowish white powder mainly composed of a tetrameric procyanidin represented by the above-shown formula (13).

PREPARATION EXAMPLE 4

1 kg Of dried root of knotgrass (*Polygonum Multiflorum*) was pulverized, added with 4 litres of 80% aqueous acetone and extracted overnight at room temperature. The liquid extract was concentrated under reduced pressure at a temperature below 30° C., then acetone was distilled off and the residue was washed with diethyl ether and extracted with ethyl acetate (400 ml$\times$3). The solvent was distilled off from the extract solution to obtain 45 g of extract. This was dissolved in 450 ml of water and fractionated by liquid chromatography on a column (60cm$\times$3.5 cm) packed with Sephadex LH-20.

In this fractionation, water and aqueous methanol were used as developing solvent and the extract was subjected to gradient elution with a water to 40% aqueous methanol system. The eluate was collected for every 1.2 liter efflux to obtain 4 fractions (fractions 1–4). Of these fractions, the lastly eluated fraction 4 was concentrated and evaporated to dryness, dissolved in ethanol and again fractionated by liquid chromatography on a column (60 cm$\times$3.5 cm$\phi$) packed with Sephadex LH-20 using ethanol (6l) as developing solvent. The eluate was fractioned into 120 fractions, 50 ml in each. The fractions 84–100 were combined and evaporated to dryness to obtain 175 mg of yellowish white powder of a dimeric procyanidin B-2 gallic acid diester represented by the above-shown formula (7).

PREPARATION EXAMPLE 5

1 kg Of fresh bark of mirica (Mirica rubra) was extracted with 4 liters of 80% aqueous acetone overnight at room temperature. The extract was concentrated under reduced pressure at a temperature below 30° C. and acetone was distilled off. The yellow crude crystal matter precipitated in the aqueous residue was removed by centrifugation (at 3,000 r.p.m. for 10 minutes), the supernatant was extracted with ethyl acetate (400 ml$\times$3), and the resulting extract was concentrated and evaporated to dryness to obtain 14.3 g of extract. This was dissolved in 100 ml of ethanol and fractionated by liquid chromatography on a column (60 cm$\times$2.5 cm$\phi$) packed with Sephadex LH-20.

For the fractionation, ethanol and aqueous ethanol were used as developing solvent and the extract was subjected to gradient elution with an ethanol to 80% aqueous ethanol system. The eluate was collected each time when its amount reached 300 ml, thus preparing 5 fractions (fractions 1–5).

The fraction 4 was concentrated and evaporated to dryness, then dissolved in 80% aqueous methanol and again fractionated by liquid chromatography on a column (60 cm$\times$3.5 cm$\phi$) packed with Sephadex LH-20 using 80% aqueous methanol (1 l) as solvent, and the eluate was fractionated into 20 fractions, 50 ml in each. The fractions 30–45 were combined and evaporated to dryness to obtain 260 mg of white powder of a dimeric prodelphinidin B-2 gallic acid diester represented by the formula (8).

Also, the fraction 2 obtained from said fractionation by the first liquid chromatography was concentrated and evaporated by dryness and again subjected to liquid chromatography on a silica gel column (60 cm$\times$3.5 cm$\phi$) by using an ethyl acetate and benzene (1:1 to 2:1) mixed solvent to obtain 95 mg of gallocatechin. Likewise, by concentrating and evaporating to dryness the fraction 3 from the fractionation by the first liquid chromatography and subjecting it to additional liquid chromatography on a polyamide column by using a water to methanol solvent, there could be obtained 620 mg of eligallocatechin gallate.

PREPARATION EXAMPLE 6

1 kg Of azuki beans (*Vigna angularis* Ohwi et Ohashi) was ground into a powder with a grain size below 12 mesh, then extracted under heating with n-hexane (10 litres$\times$2) for one hour for defatting and further subjected to heat extraction with 70% aqueous acetone (10 litres$\times$2). The extract was concentrated under reduced pressure at a temperature below 40° C. and acetone was distilled off. Water was added to the residue to form an aqueous solution of 4 litres and this solution was washed with diethyl ether (3 liters$\times$3), then brought into a saturated state by adding sodium chloride and extracted with ethyl acetate (4 litres$\times$3).

The extract was concentrated under reduced pressure at a temperature below 40° C. and evaporated to dryness. The residue was added with 10 ml of ethyl acetate and the insolubles were filtered off. The thus obtained clean solution was added dropwise with a double volume of chloroform and the resultantly formed white precipitate was collected by filtration and dried to obtain 550 mg of yellowish white powder mainly composed of a mixture of dimeric to tetrameric proanthocyanidins.

The antioxidant action and effects of the proanthocyanidins produced as described above are shown below by way of test examples.

TEST EXAMPLE 1

A commercially sold salad oil (a product by Showa Sangyo Co., Ltd.) was pipetted 5 ml each into test tubes. Then various kinds of proanthocyanidins shown in Table 1 below were added thereto a concentration of 0.2 mg/ml and dissolved by stirring. The test tubes were kept in an 180° C. thermostatic oil bath and oxygen gas was bubbled into them at a rate of 2 ml/sec. 40 mintues thereafter, the amount of lipid peroxide in the salad oil was measured by the method shown in Yagi's Vitamins, Vol. 49, pp. 403–405. The results are shown in Table 1.

Used as controls were said salad oil added with no proanthocyanidin (control I) and those added with a commercial catechin, a gallocatechin obtained as a byproduct in Preparation Example 5 and an epigallocatechin gallate, which are the monomers forming a structural unit of proanthocyanidins (control II). These control salad oil samples were similarly treated and the amount of lipid peroxide was similarly measured, the results being shown in Table 1.

The lipid peroxide inhibition rate of the additives of this invention and the control additives in said treatment was calculated from these results and also shown in Table 1.

TABLE 1

| | Additive | Structural formula* | Amount of lipid peroxide | Lipid peroxide rise inhibition rate (%)** |
|---|---|---|---|---|
| This invention | Dimeric procyanidin B-2 | (1) | 22.4 | 75 |
| | Dimeric procyanidin A-2 | (3) | 25.0 | 70 |
| | Dimeric prodelphinidin B-3 | (5) | 17.2 | 85 |
| | Trimeric prodelphinidin | (10) | 22.9 | 74 |
| | Tetrameric procyanidin | (13) | 29.1 | 62 |
| | Dimeric procyanidin B-2 gallic acid diester | (7) | 10.5 | 98 |
| | Dimeric prodelphinidin B-2 gallic acid diester | (8) | 10.1 | 100 |
| | Mixture of dimeric to tetrameric proanthocyanidins from adzuki beans | — | 36.4 | 48 |
| | Mixture of pentameric to decimeric proanthocyanidins from adzuki beans | — | 52.5 | 17 |
| Control I | No proanthocyanidin added | — | 65.2 | 0 |
| Control II | Commercial d-catechin | — | 54.7 | 12 |
| | Gallocatechin | — | 44.7 | 32 |
| | Epigallocatechin gallate | — | 45.0 | 35 |
| Non-treated | — | — | 10.1 | — |

*Structural formula No. given in the text.

**Lipid peroxide rise inhibition rate (%) = $\frac{A - B}{A} \times 100$

A: (amount of lipid peroxide in salad oil with no proanthocyanidin added) − (amount of lipid peroxide in non-treated salad oil)
B: (amount of lipid peroxide in salad oil with additive) − (amount of lipid peroxide in non-treated salad oil)

TEXT EXAMPLE 2

50 kg Of a commercially sold frying oil (a product by Showa Sangyo KK) was taken into a 100 ml thick-type test tube. Then 3.5 g of Tween 80 and 0.1 g of a mixture of dimeric to tetrameric proanthocyanidins from adzuki beans prepared in Preparation Example 6 were added and dissolved in said frying oil by stirring. This test tube were kept in a 100° C. thermostatic oil bath and aerated by an air pump, the material therein being sampled at intervals of three hours. The peroxide value (POV) of the respective samples collected until 18 hours have elapsed (from the moment of insertion of the test tube into the 100° C. oil bath) was determined by the method shown in General Pharmaceutical Test Methods and Expositions, compiled by Japan Pharmaceutical Society, 6th Ed., pp. 61–62 (1976). The test results are shown in Table 2.

Used as a control was said frying oil with no proanthocyanidin mixture added. This control frying oil was similarly treated and POV of each sample collected in the same manner as described above was similarly determined. The results are shown in Table 2.

The POV rise inhibition rate of the additive of this invention after the passage of 18 hours was calculated from the POV of the samples of this invention and the control samples after the passage of 18 hours, and the results were also shown in Table 2.

TABLE 2

| Samples | Treating time (hr.) | | | | | | | POV rise* inhibition rate (%) |
|---|---|---|---|---|---|---|---|---|
| | 0 | 3 | 6 | 9 | 12 | 15 | 18 | |
| This invention | 5 | 5 | 5 | 6 | 9 | 13 | 22 | 0 |
| Control | 5 | 15 | 34 | 50 | 75 | 106 | 129 | 86.2 |

*POV rise inhibition rate (%) = $\frac{A - B}{A} \times 100$

A: rise of POV in control (POV after 18 hrs.) − (POV at start)
B: rise of POV in samples of this invention (POV after 18 hrs.) − (POV at start)

TEST EXAMPLE 3

300 g Of lard was heated to form a liquid state, and in this liquid lard was added and dissolved 0.6 g of a mixture of dimeric to tetrameric proanthocyanidins from adzuki beans prepared in Preparation Example 6. Then 1.5 kg of wheat flour, 600 g of sugar, 7.5 g of sodium chloride, 7.5 g of sodium bicarbonate and 7.5 g of ammonium carbonate was added thereto and mixed well with water to form a rather hard dough. This dough was punched into pieces of 4 cm in diameter and 0.3 cm in thickness and baked at 180° C. for 5 minutes to make biscuits.

1 kg Of these test biscuits and 1 kg of control biscuits made from the same materials and the same treatment as described above except for use of lard not added with said proanthocyanidin mixture were placed respectively in polyethylene film bags. Each bag was left in a 37° C. thermostat and an organoleptic test by 12 skilled persons was made on the change (deterioration) of flavor of the biscuits upon passage of every three days.

As a result, an obvious deterioration of flavor due to oxidation of lard was noted in the control biscuits 6 days after packed in the polyethylene bag, while the test biscuits showed no deterioration of flavor even after passage of 12 days.

From the results shown in Tables 1 and 2, it is apparent that the proanthocyanidins of this invention have a stronger antioxidant action against fats and oils and a longer duration of such action than the monomers, such as catechin, which form a structural unit of said proanthocyanidins and which are known to have an antioxidant action. Also, the proanthocyanidins of this invention have no problem regarding safety in use as they are obtained from the natural sources, and further, a apparent from the results of Test Example 3, they are effective for preventing deterioration of quality of the foods, etc., containing fats and oils during their storage.

What is claimed is:

1. A method for inhibiting the oxidation of edible fats and oils in compositions containing said edible fats and oils which comprises adding to said composition about 0.001 to 2% by weight of a proanthocyanidin compound which exhibits an antioxidant action, said proanthocyanidin compound being selected from the group consisting of a dimeric procyanidin B-2 and its stereoisomers represented by formula (1)

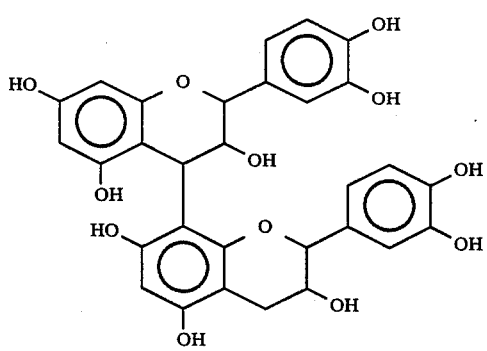

a dimeric procyanidin represented by formula (2)

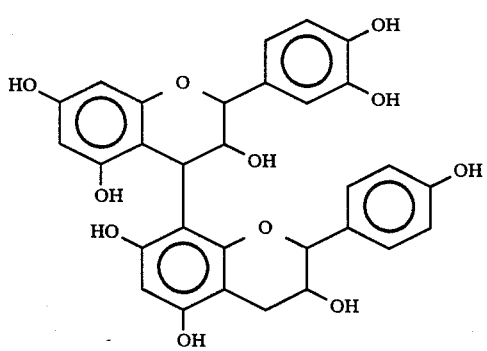

a dimeric proanthocyanidin A-2 and its stereoisomers represented by formula (3)

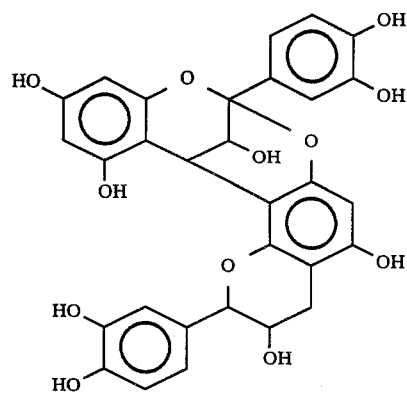

a dimeric procyanidin represented by formula (4)

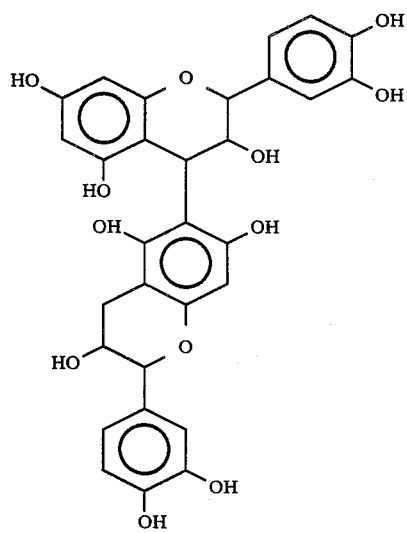

a dimeric prodelphinidin represented by formula (5)

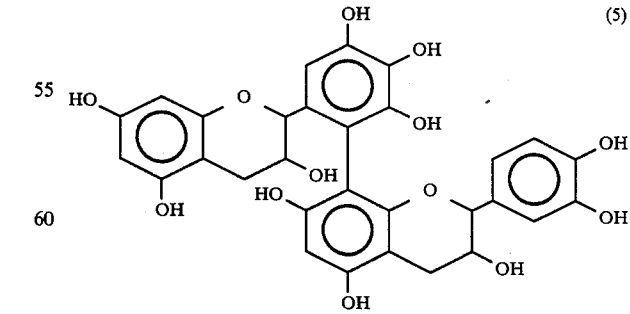

a dimeric procyanidin B-1 gallate and its stereoisomers represented by formula (6)

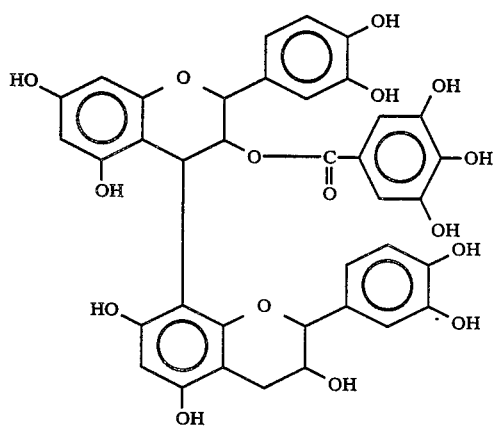

a dimeric procyanidin B-1 gallate and its stereoisomers represented by formula (6)

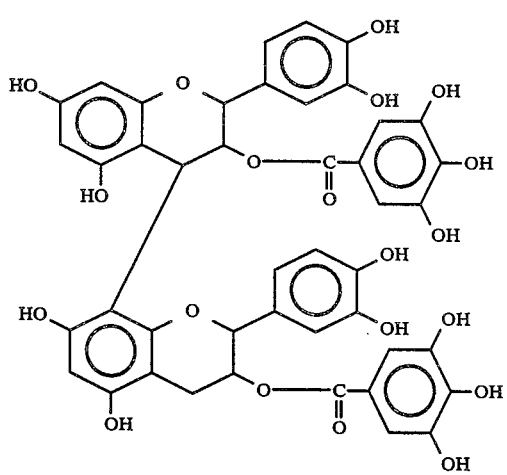

a dimeric prodelphinidin B-2 gallate and its stereoisomers represented by formula (7)

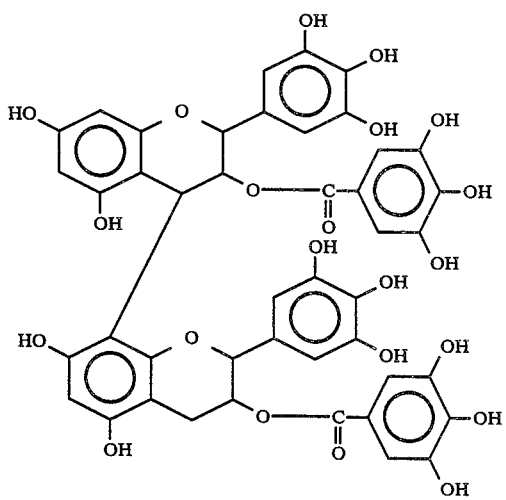

a dimeric propelargonidin represented by formula (8)

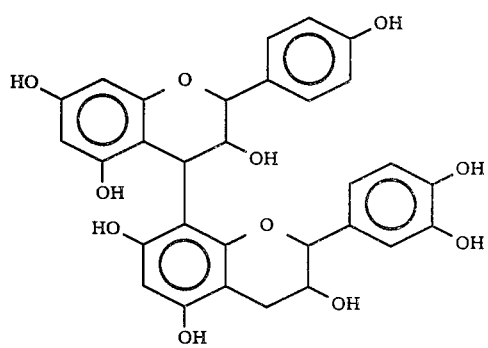

a trimeric prodelphinidin represented by formula (9)

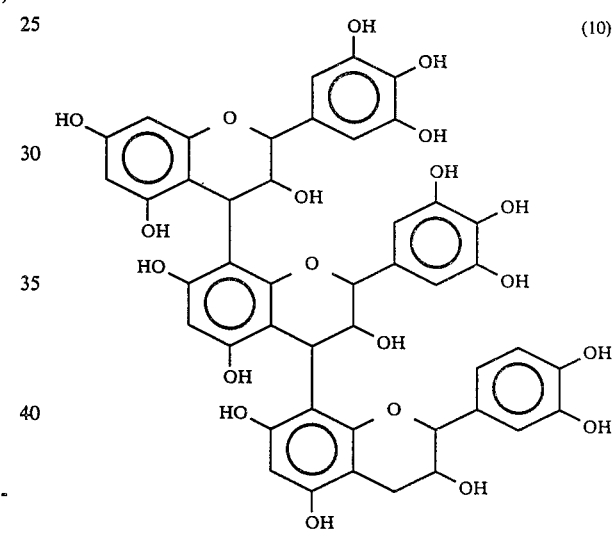

a dimeric procyanidin represented by formula (10)

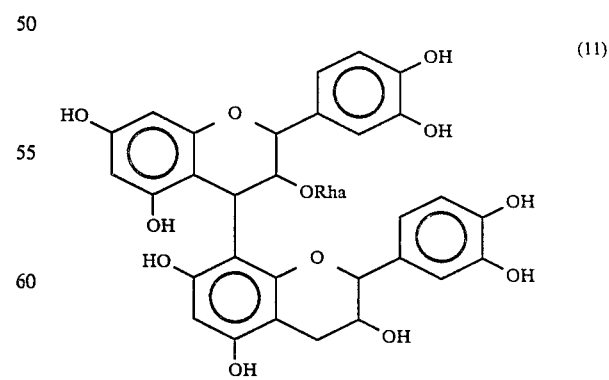

wherein Rha is rhamnose a propelargonidin represented by formula (11)

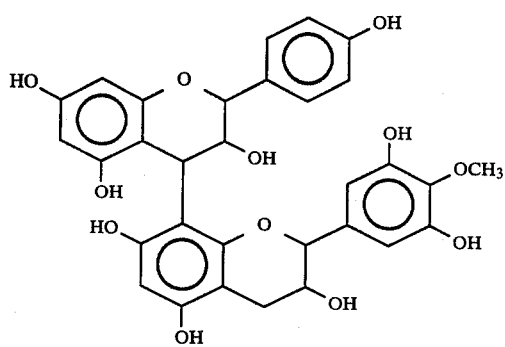

a tetrameric proanthocyanidin represented by formula (13)

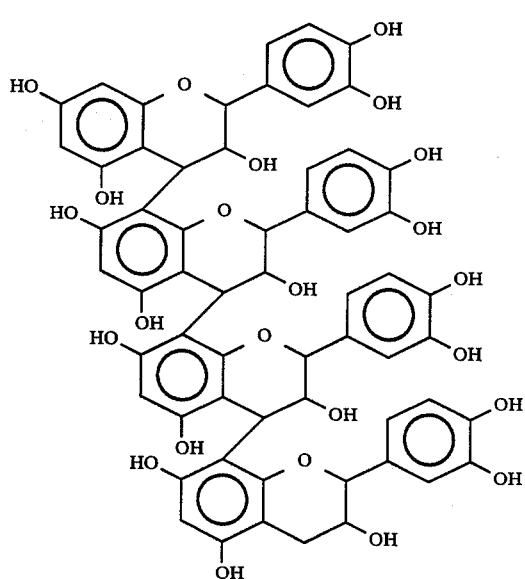

and mixtures thereof.

2. A method for inhibiting the oxidation of fats and oils in food compositions and cosmetric preparations which comprises adding to said food compositions or cosmetic preparations about 0.001 to 2% by weight of a proanthocyanidin compound which exhibits an antioxidant action, said proanthocyanidin compound being selected from the group consisting of a dimeric procyanidin B-2 and its stereoisomers represented by formula (1)

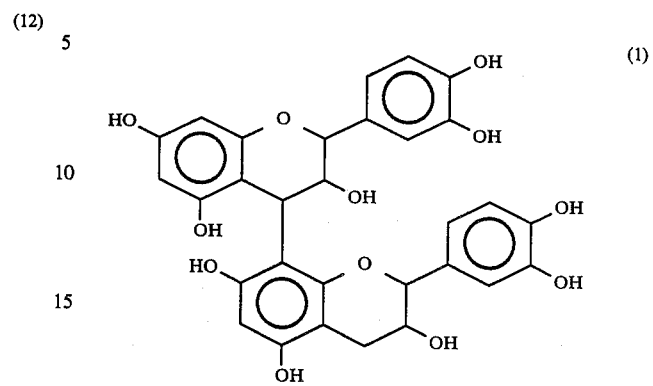

a dimeric procyanidin represented by formula (2)

a dimeric proanthocyanidin A-2 and its stereoisomers represented by formula (3)

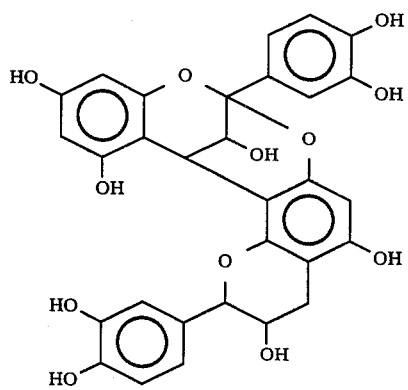

a dimeric procyanidin represented by formula (4)

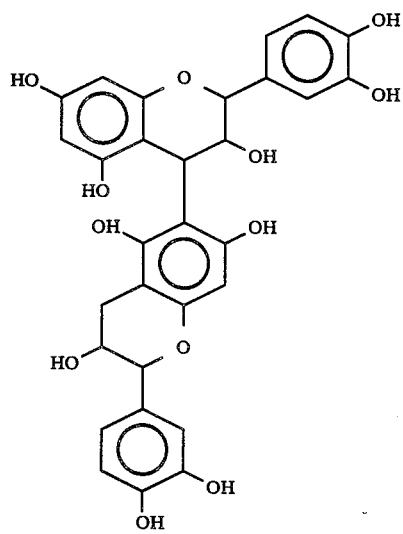

a dimeric prodelphinidin represented by formula (5)

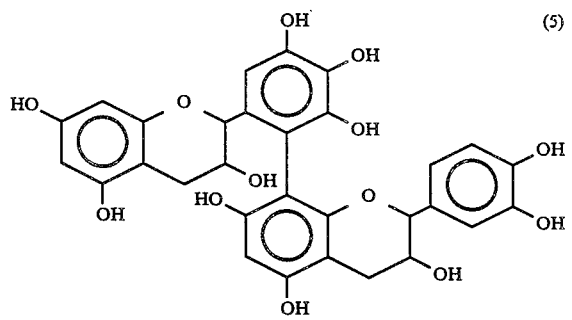

a dimeric procyanidin B-1 gallate and its stereoisomers represented by formula (6)

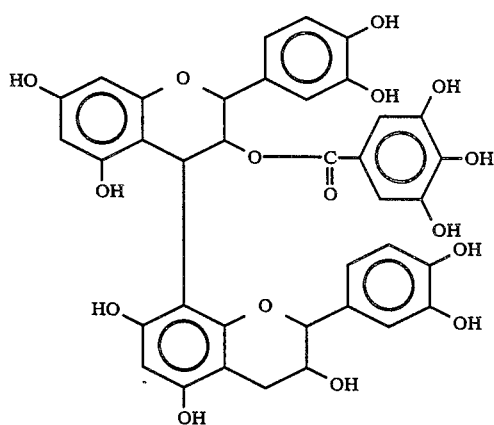

a dimeric procyanidin B-1 gallate and its stereoisomers represented by formula (7)

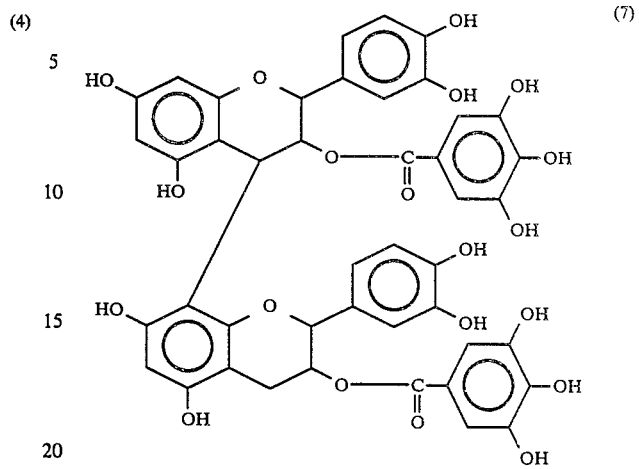

a dimeric prodelphinidin B-2 gallate and its stereoisomers represented by formula (8)

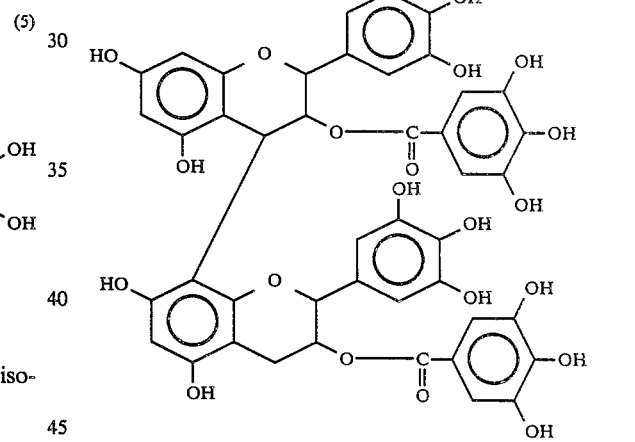

a dimeric propelargonidin represented by formula (9)

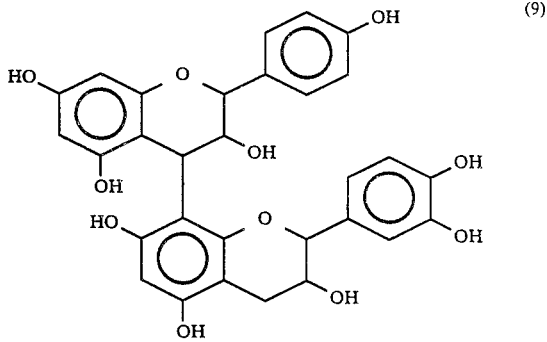

a trimeric prodelphinidin represented by formula (10)

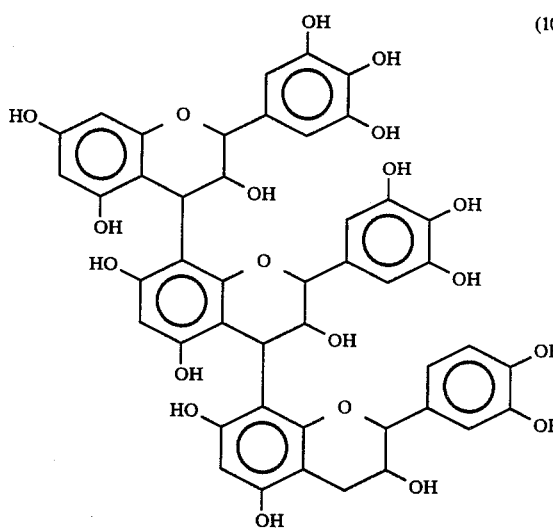

a dimeric procyanidin represented by formula (11)

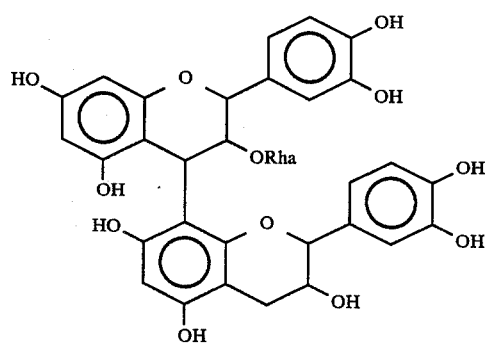

wherein Rha is rhamnose a propelargonidin represented by formula (12)

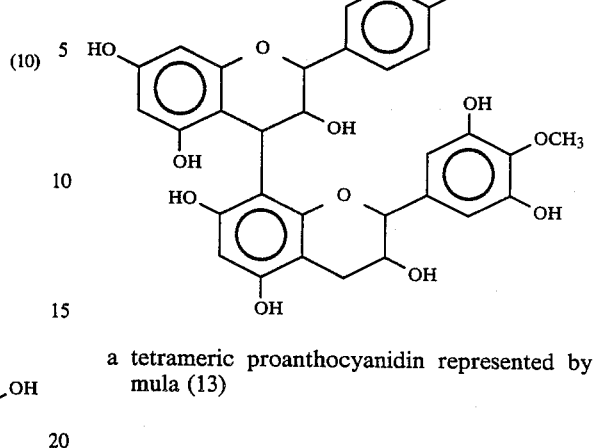

a tetrameric proanthocyanidin represented by formula (13)

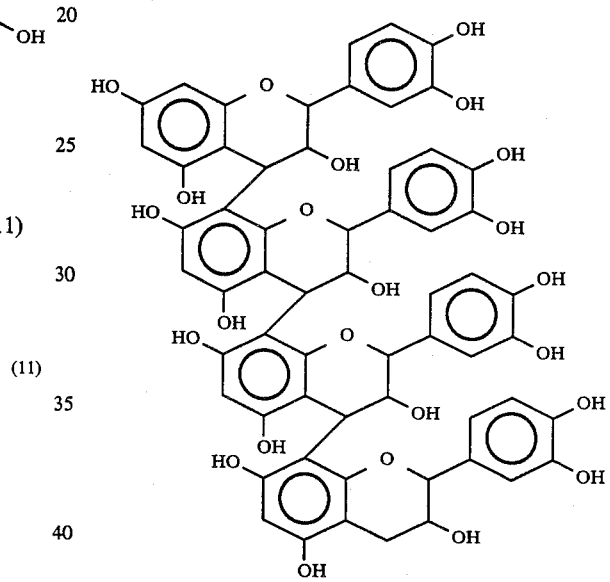

and mixtures thereof.

3. The method of claim 1 wherein said proanthocyanidin compound is added to said edible fats and oils as a powder, as an aqueous solution or as an alcoholic solution.

4. The method of claim 2 wherein said proanthocyanidin compound is added to said food compositions or cosmetic preparations as a powder, as an aqueous solution or as an alcoholic solution.

* * * * *